(12) United States Patent
Exner et al.

(10) Patent No.: US 8,039,216 B2
(45) Date of Patent: *Oct. 18, 2011

(54) METHODS FOR DETECTING NUCLEIC ACIDS USING MULTIPLE SIGNALS

(75) Inventors: Maurice Exner, Mission Viejo, CA (US); Amy Rogers, Dana Point, CA (US)

(73) Assignee: Quest Diagnostics Investments Incorporated, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 12/845,465

(22) Filed: Jul. 28, 2010

(65) Prior Publication Data

US 2010/0291583 A1 Nov. 18, 2010

Related U.S. Application Data

(63) Continuation of application No. 11/337,805, filed on Jan. 23, 2006, now Pat. No. 7,785,786.

(51) Int. Cl.
*C12Q 1/68* (2006.01)
*C12P 19/34* (2006.01)
*C07H 21/04* (2006.01)

(52) U.S. Cl. ............ 435/6.12; 435/91.2; 536/24.312; 536/24.32; 536/24.33

(58) Field of Classification Search ........ 435/6; 536/22.1
See application file for complete search history.

(56) References Cited

U.S. PATENT DOCUMENTS

| | | |
|---|---|---|
| 5,582,989 A | 12/1996 | Caskey et al. |
| 5,702,901 A | 12/1997 | Cummins et al. |
| 5,733,751 A | 3/1998 | Cummins et al. |
| 5,744,299 A | 4/1998 | Henrickson et al. |
| 5,811,295 A | 9/1998 | Cummins et al. |
| 5,871,908 A | 2/1999 | Henco et al. |
| 5,994,056 A | 11/1999 | Higuchi |
| 6,015,664 A | 1/2000 | Henrickson et al. |
| 6,030,115 A | 2/2000 | Ishiguro et al. |
| 6,140,054 A | 10/2000 | Wittwer et al. |
| 6,171,785 B1 | 1/2001 | Higuchi |
| 6,174,668 B1 | 1/2001 | Cummins et al. |
| 6,174,670 B1 * | 1/2001 | Wittwer et al. ............ 435/6 |
| 6,197,520 B1 | 3/2001 | Wittwer et al. |
| 6,472,156 B1 | 10/2002 | Wittwer et al. |
| 6,569,627 B2 | 5/2003 | Wittwer et al. |
| 6,605,451 B1 * | 8/2003 | Marmaro et al. ............ 435/91.2 |
| 6,881,835 B2 | 4/2005 | Bai et al. |
| 6,936,415 B1 | 8/2005 | Cummins et al. |
| 7,785,786 B2 * | 8/2010 | Exner et al. ............ 435/6 |
| 2003/0165859 A1 | 9/2003 | Nazarenko et al. |
| 2004/0002098 A1 | 1/2004 | Wittwer et al. |
| 2004/0053230 A1 | 3/2004 | Schaffer et al. |
| 2004/0175752 A1 | 9/2004 | Schaffer et al. |
| 2004/0253582 A1 | 12/2004 | Henrickson et al. |
| 2006/0029965 A1 | 2/2006 | Wittwer et al. |

FOREIGN PATENT DOCUMENTS

| | | |
|---|---|---|
| WO | WO-97/46714 | 12/1997 |
| WO | WO-00/14278 | 3/2000 |
| WO | WO-00/14279 | 3/2000 |
| WO | WO-02/097132 | 12/2002 |
| WO | WO 02097132 A2 * | 12/2002 |
| WO | WO-03/043402 | 5/2003 |
| WO | WO-2005/040425 | 5/2005 |
| WO | WO-2005/047470 | 5/2005 |
| WO | WO-2005/098031 | 10/2005 |

OTHER PUBLICATIONS

Abu-Halaweh et al., Rapid detection and differentiation of pathogenic *Campylobacter jejuni* and *Campylobacter coli* by real time PCR. Research in Microbiology, 156: 107-114, 2005.
Beuret, "Simultaneous Detection of Enteric Viruses by Multiplex Real-Time RT-PCR," J. Virol. Methods, 115:1-8 (2004).
Bohling et al., "Rapid Simultaneous Amplification and Detection of the MBR/JH Chromosomal Translocation by Fluorescence Melting Curve Analysis," Am. J. Path. 154:97-103 (1999).
Boivin et al., "Multiplex Real-Time PCR Assay for Detection of Influenza and Human Respiratory Syncytial Viruses," J. Clin. Micro., 42:45-51 (Jan. 2004).
Dempsey et al., "Detection of Five Common CFTR Mutations by Rapid-Cycle Real-Time Amplification Refractory Mutation System PCR," Clin. Chem., 50:4, 773-775 (2004).
Echevarria et al., "Simultaneous Detection and Identification of Human Parainfluenza Viruses 1, 2, and 3 from Clinical Samples by Multiplex PCR," J. Clin. Micro., 36:1388-1391 (May 1998).
Elenitoba-Johnson et al., "Multiplex PCR by Multicolor Fluorimetry and Fluorescence Melting Curve Analysis," Nature Medicine, 7:249-253 (Feb. 2001).

(Continued)

*Primary Examiner* — Prabha Chunduru
(74) *Attorney, Agent, or Firm* — Foley & Lardner LLP

(57) ABSTRACT

Disclosed is are methods for identifying a nucleic acid in a sample. In one example, the method includes: (a) contacting the nucleic acid in the sample with an oligonucleotide that is specific for the nucleic acid in the sample and that is labeled with at least a first fluorescent dye; (b) contacting the nucleic acid in the sample with a second fluorescent dye that is different from the first fluorescent dye, such that the second fluorescent dye interacts with the nucleic acid; (c) amplifying the nucleic acid if present in the sample; and (d) detecting the nucleic acid if present in the sample by observing fluorescence from the first fluorescent dye after the oligonucleotide hybridizes to the amplified nucleic acid and determining the melting temperature of the amplified nucleic acid by measuring the fluorescence of the second fluorescent dye. The second fluorescent dye may include a fluorescent intercalating agent.

24 Claims, No Drawings

OTHER PUBLICATIONS

Giglio et al., "Demonstration of Preferential Binding of SYBR Green I to Specific DNA Fragments in Real-Time Multiplex PCR," Nucl. Acids. Res. 31:e136 (2003).

Grace et al., "Development and Assessment of a Quantitative Reverse Transcription-PCR Assay for Simultaneous Measurement of Four Amplicons," Clin. Chem. 49:9, 1467-1475 (2003).

Gundry et al., "Amplicon Melting Analysis with Labeled Primers: A Closed-Tube Method for Differentiating Homozygotes and Heterozygotes," Clin. Chem., 49:3, 396-406 (2003).

Herrmann et al., "Rapid β-Globin Genotyping by Multiplexing Probe Melting Temperature and Color," Clin. Chem., 46:3, 425-430 (2000).

Howell et al., "iFRET: An Improved Fluorescence System for DNA-Melting Analysis," Genome Research, 12:1401-1407 (2002).

Howell, et al, iFRET: An improved Flouorescence system for DNA-melting analysis, (2002), Genome Research, 12:1401-1407.

International Search Report dated Feb. 6, 2008 in application PCT/US2007/001859.

Jobs et al., "DASH-2: Flexible, Low-Cost, and High-Throughput SNP Genotyping by Dynamic Allele-Specific Hybridization on Membrane Arrays," Genome Research, 13:916-924 (2003).

Myakishev, et al, High-throughput SNP genotyping by allele-specifc PCR with universal energy-tranfer-labeled primers, (2001), Gen Res, 11:163-169.

Nakayama et al., Single-nucleotide polymorphism analysis using fluorescence resonance energy transfer between DNA-labeling fluorophore, fluorescein isothiocyanate and DNA intercalator, POPO-3, on bacterial magnetic particles. Biotechnology and Bioengineering, 84:96-102, 2003.

Schütz et al., "Genotyping of Eight Thiopurine Methyltransferase Mutations: Three-Color Multiplexing, "Two-Color/Shared" Anchor, and Fluorescence-quenching Hybridization Probe Assays Based on Thermodynamic Nearest-Neighbor Probe Design," Clin. Chem. 46:11, 1728-1737 (2000).

Talavera et al., Fluorescence energy transfer between fluorescein label and DNA intercalators to detect nucleic acids hybridization in homogeneous media. Applied Spectroscopy, 57(2):208-215, 2003.

Templeton et al., "Rapid and Sensitive Method Using Multiplex Real-Time PCR for Diagnosis of Infections by Influenza A and Influenza B Viruses, Respiratory Syncytial Virus, and Parainfluenza Viruses 1, 2, 3, and 4," J. Clin. Micro., 42:1564-1569 (Apr. 2004).

Vet et al., "Multiplex Detection of Four Pathogenic Retroviruses Using Molecular Beacons," PNAS, 96:6394-99 (May 1999).

Wang et al., Fluorescein provides a resonance gate for FRET from conjugated polymers to DNA intercalated dyes. Journal of the American Chemical Society, 126:5446-5451, 2004.

Wittwer et al., "High-Resolution Genotyping by Amplicon Melting Analysis Using LCGreen," Clin. Chem., 49:6, 853-860 (2003).

Wittwer et al., "Real-Time Multiplex PCR Assays," Methods 25, 430-442 (2001).

Zhou et al., "Closed-Tube Genotyping with Unlabeled Oligonucleotide Probes and a Saturating DNA Dye," Clin. Chem., 50:8, 1328-1335 (2004).

\* cited by examiner

METHODS FOR DETECTING NUCLEIC ACIDS USING MULTIPLE SIGNALS

CROSS-REFERENCE TO RELATED APPLICATIONS

This application is a continuation of U.S. application Ser. No. 11/337,805, filed Jan. 23, 2006, hereby incorporated by reference in its entirety.

BACKGROUND

The present methods relate generally to the field of identifying nucleic acids. In particular, the present methods relate to the field of identifying nucleic acids in a sample by detecting multiple signals such as signals emitted from fluorophores. The present methods also relate to the field of identifying nucleic acid in a sample by using labeled oligonucleotides to detect the nucleic acid in combination with agents for determining the melting temperature of the detected nucleic acid.

Methods for detecting nucleic acids such as multiplex methods are increasing important in medical diagnostics. Typical multiplex methods utilize PCR amplification, and in particular, real-time quantitative PCR. Real-time or end-point detection methods for PCR typically are based on one of two principles for monitoring amplification products: (1) specific hybridization by probes or primers to single-stranded DNA; or (2) binding by small molecules (e.g., intercalating agents) to double-stranded DNA. Probes and primers may include Molecular Beacon Probes, Scorpion® Primers, Taqman® Probes, and other labeled primers or probes. Small molecules that bind to DNA may include intercalators (e.g., SYBR™ Green I dye and ethidium bromide) and minor groove binders.

Methods for detecting nucleic acid that utilize probes and primers typically involve labeling each probe or primer with a unique label (e.g., a fluorescent dye). Because multiplexing methods commonly utilize fluorescent dyes, they often are called "color multiplexing" methods. These types of multiplexing methods are limited by the practical number of labels that can be detected and distinguished in a reaction mixture. When fluorescent dyes are used in these methods, typically no more than four (4) different dyes can be detected and distinguished based on the dyes' specific absorption (excitation) maximum wavelengths and emission maximum lengths using current detection technology.

Methods for detecting nucleic acid that utilize small binders such as intercalators typically involve determining melting temperatures ("$T_m$") to detect a target nucleic acid. As such, multiplexing methods that utilize this technology often are called "$T_m$ multiplexing" methods. These methods may include determining the melting temperature of a complex formed by a probe and the amplified target nucleic acid, or determining the melting temperature of the amplified target nucleic acid itself (i.e., the amplicon). Where an intercalator is utilized, typically the intercalator exhibits a change in fluorescence based on whether the detected nucleic acid is double-stranded or single-stranded. These methods may be limited in that intercalating agents interact with double-stranded nucleic acids non-specifically, and as such, multiple detected products must be distinguished by criteria such as resolvable melting temperatures.

Methods for detecting a nucleic acid have been described in which a fluorescent intercalator is used as a donor for fluorescence resonance energy transfer (FRET) together with a fluorescently labeled oligonucleotide probe as an acceptor for FRET. See Howell et al., "iFRET: An Improved Fluorescence System for DNA-Melting Analysis," GENOME RESEARCH 12:1401-1407 (2002). However, these described methods require that the intercalator and the fluorescently labeled oligonucleotide probe be selected to permit FRET. Further, these methods do not involve directly observing a signal from an intercalator as an indication of the melting temperature of an amplified nucleic acid (i.e., an amplicon). Rather, iFRET involves indirectly observing a signal from an intercalator (via FRET) as an indication of the melting temperature of a complex formed between the amplified nucleic acid and a fluorescently labeled oligonucleotide probe.

By combining detection methods based on color and melting temperature (e.g., color multiplexing and $T_m$ multiplexing methods), it may be possible to detect a plurality of nucleic acids in a sample, Such methods may be useful in diagnostic methods related to identifying human pathogens (e.g., viruses that may include respiratory pathogens such as human parainfluenza virus).

SUMMARY OF THE INVENTION

Disclosed are methods for identifying a nucleic acid in a sample. Typically, the methods include detecting multiple signals such as signals emitted from fluorophores. In the disclosed methods, fluorophores may be used to label oligonucleotides that are specific for nucleic acid in the sample. In addition, fluorophores in the method may include fluorophores that interact with the nucleic acid and are used to identify the nucleic acid based on the melting temperature of the nucleic acid.

In some embodiments, the methods include identifying a nucleic acid in a sample by performing steps that include: (a) contacting the nucleic acid in the sample with an oligonucleotide that is specific for the nucleic acid and that is labeled with at least a first fluorescent dye; (b) contacting the nucleic acid with a second fluorescent dye that is different from the first fluorescent dye and that interacts with the nucleic acid; (c) amplifying the nucleic acid if the nucleic acid is present in the sample; and (d) detecting the nucleic acid if the nucleic acid is present in the sample by observing fluorescence from the first fluorescent dye after the oligonucleotide hybridizes to the amplified nucleic acid (e.g., as a probe) and/or after the oligonucleotide is incorporated into the amplified nucleic acid (e.g., as a primer); and determining the melting temperature of the amplified nucleic acid by measuring the fluorescence of the second fluorescent dye. Nucleic acid identified in the method may include DNA or RNA, which may be single-stranded or double-stranded. DNA may include cDNA prepared from RNA (e.g., cDNA prepared by reverse transcribing mRNA).

In other embodiments, the methods may include identifying one of two or more nucleic acids potentially in a sample by performing the following steps: (a) contacting the nucleic acids in the sample with two or more oligonucleotides, each of which is specific for a different one of the two or more nucleic acids in the sample and each of which is labeled with at least one fluorescent dye; (b) contacting the nucleic acids in the sample with a different fluorescent dye from the fluorescent dye that is used to label the two or more oligonucleotides, such that the different fluorescent dye interacts with the two or more nucleic acids; (c) amplifying at least one of the two or more nucleic acids; and (d) detecting the amplified nucleic acid if present in the sample by observing fluorescence from the fluorescent dye of at least one of the two or more oligonucleotides after hybridized to the amplified nucleic acid (e.g., as a probe) and/or after incorporated into the amplified nucleic acid (e.g., as a primer); and determining the melting temperature of the amplified nucleic acid by measuring the fluorescence of the different fluorescent dye that interacts with the amplified nucleic acid. The oligonucleotides may be labeled with the same or different fluorescent dyes. Where the oligonucleotides are labeled with the same fluorescent dye, preferably two or more amplified products have melting temperatures that differ from each other by at least about 1° C., more preferably by at least about 2° C., or even more preferably by at least about 4° C.

In further embodiments, the methods may include identifying two or more nucleic acids potentially in a sample by performing the following steps: (a) contacting the nucleic acids in the sample with two or more oligonucleotides, each of which are specific for a different one of the two or more nucleic acids and each of which is labeled with a fluorescent dye; (b) contacting the nucleic acids in the sample with a different fluorescent dye from the fluorescent dye that is used to label the two or more oligonucleotides, such that the different fluorescent dye interacts with the two or more nucleic acids; (c) amplifying the two or more nucleic acids; and (d) detecting the two or more nucleic acids if present in the sample by (i) observing fluorescence from each fluorescent dye of the two or more oligonucleotides after hybridized to the amplified two or more nucleic acids (e.g., as probes) and/or after incorporated into the amplified two or more nucleic acids (e.g., as primers); and (ii) separating the two or more amplified nucleic acids from each other and determining the melting temperature of the separated two or more nucleic acids by measuring the fluorescence of the different fluorescent dye that interacts with each of the separated two or more nucleic acids. The oligonucleotides may be labeled with the same or different fluorescent dyes. Where the oligonucleotides are labeled with the same fluorescent dye, preferably the amplified product has a melting temperature that differs from the melting temperature of any other potentially amplified nucleic acid by at least about 1° C., more preferably by at least about 2° C., or even more preferably by at least about 4° C. The two or more amplified nucleic acids may be separated by any suitable method. For example, separating the two or more amplified nucleic acids from each other may include hybridization methods, such as physical separation methods related to the molecular weight of the amplified product or probe capture methods.

The steps of the methods disclosed above may be performed concurrently or in any suitable order. In some embodiments, step (a) and step (b) are performed concurrently. In other embodiments, step (a) is performed before step (b), or alternatively, step (b) is performed before step (a). In some embodiments, step (c) is performed before or during step (a), and/or step (c) is performed before or during step (b). In some embodiments, step (d) is performed during step (c).

Also disclosed are methods for identifying nucleic acid in a sample by performing the following steps: (a) reacting a mixture that includes (i) the sample, (ii) at least one oligonucleotide that is labeled with at least one fluorescent dye and that is specific for at least one nucleic acid in the sample; and (iii) an intercalating agent such as a fluorescent dye that is different from the at least one fluorescent dye that labels the at least one oligonucleotide; (b) detecting fluorescence from at least the one fluorescent dye that labels the at least one oligonucleotide; and (c) detecting fluorescence directly from the fluorescent dye of the intercalating agent. Fluorescence from the at least one fluorescent dye that labels the at least one oligonucleotide may be detected when the oligonucleotide hybridizes to the amplified nucleic acid (e.g., as a probe) and/or when the oligonucleotide is incorporated into the amplified nucleic acid (e.g., as a primer). Optionally, the reaction mixture may include an amplification reaction mixture, and optionally, the methods may include amplifying the nucleic acid present in the sample. Further, these methods may include determining the melting temperature of the amplified nucleic acid (e.g., by detecting fluorescence directly from the fluorescent dye of the intercalating agent at a gradient of temperatures). The steps of the methods may be performed concurrently or in any suitable order.

The oligonucleotides that are used in the disclosed methods may be suitable as primers for amplifying at least one nucleic acid in the sample and/or as probes for detecting at least one nucleic acid in the sample. In some embodiments, the oligonucleotides are labeled with at least one fluorescent dye, which may produce a detectable signal. The fluorescent dye may function as a fluorescence donor for fluorescence resonance energy transfer (FRET). The oligonucleotides also may be labeled with a second fluorescent dye or a quencher dye that may function as a fluorescence acceptor (e.g., for FRET). Where the oligonucleotide is labeled with a first fluorescent dye and a second fluorescent dye, a signal may be detected from the first fluorescent dye, the second fluorescent dye, or both.

The oligonucleotides may be capable of forming intramolecular structures such as an intramolecular hairpin. In some embodiments, the oligonucleotides are labeled with a fluorescent dye as a donor, and a either a second fluorescent dye or a quencher dye as an acceptor, where FRET is capable of occurring between the donor and acceptor when the oligonucleotides form intramolecular hairpin structures. In some embodiments, the oligonucleotide may be designed such that fluorescence from the acceptor is induced or fluorescence from the donor is dequenched after the oligonucleotide hybridizes to a target nucleic acid.

Typically, the oligonucleotide emits a detectable signal after the oligonucleotide hybridizes to a target nucleic acid (e.g., as a probe or primer that exhibits fluorescence induction or dequenching). In some embodiments, the oligonucleotide may hybridize to a target nucleic acid and emit a detectable signal after the oligonucleotide is hydrolyzed during amplification of the target nucleic acid (e.g., as a hydrolyzed probe that exhibits fluorescence dequenching). In further embodiments, the oligonucleotide may hybridize to a target nucleic acid and emit a detectable signal after the oligonucleotide is incorporated into an amplified nucleic acid (e.g., as primer that exhibits fluorescence induction or dequenching).

In some embodiments, the method may include identifying a nucleic acid in a sample without observing FRET between any fluorescent dye that labels one oligonucleotide and any other fluorescent dye that labels another oligonucleotide. Further, the method may include identifying a nucleic acid in a sample without observing FRET between the fluorescent dye that is used to determine the melting temperature of the detected nucleic acid and any of the fluorescent dyes that label the plurality of oligonucleotides that are specific for nucleic acids in the sample.

The methods typically include determining the melting temperature of a nucleic acid (e.g., an amplified nucleic acid), which may be used to identify the nucleic acid. Where the oligonucleotides of the method are labeled with a first fluorescent dye, determining the melting temperature of the detected nucleic acid may include observing a signal from a second fluorescent dye that is different from the first fluorescent dye without observing fluorescence resonance energy transfer between the first fluorescent dye and the second fluorescent dye.

In some embodiments, the second fluorescent dye for determining the melting temperature of the detected nucleic acid is an intercalating agent. Suitable intercalating agents may include, but are not limited to SYBR™ Green 1 dye, SYBR dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, and mixture thereof. In suitable embodiments, the selected intercalating agent is SYBR™ Green 1 dye.

Typically, an intercalating agent used in the method will exhibit a change in fluorescence when intercalated in double-stranded nucleic acid. A change in fluorescence may include an increase in fluorescence intensity or a decrease in fluorescence intensity. For example, the intercalating agent may exhibit a increase in fluorescence when intercalated in double-stranded nucleic acid, and a decrease in fluorescence when the double-stranded nucleic acid is melted. A change in fluorescence may include a shift in fluorescence spectra (i.e., a shift to the left or a shift to the right in maximum absorbance wavelength or maximum emission wavelength). For example, the intercalating agent may emit a fluorescent signal of a first wavelength (e.g., green) when intercalated in double-stranded nucleic and emit a fluorescent signal of a second wavelength (e.g., red) when not intercalated in double-stranded nucleic acid. A change in fluorescence of an intercalating agent may be monitored at a gradient of temperatures to determine the melting temperature of the nucleic acid (where the intercalating agent exhibits a change in fluorescence when the nucleic acid melts).

In the disclosed methods, oligonucleotides that are specific for different target nucleic acids may be labeled with the same fluorescent dye. In some embodiments, each of these different target nucleic acids may have different melting temperatures. For example, each of these different target nucleic acids may have a melting temperature that differs by at least about 1° C. more preferably by at least about 2° C., or even more preferably by at least about 4° C. from the melting temperature of any of the other different target nucleic acids which may be detected by observing fluorescence from the same fluorescent dye.

The method may be performed in any suitable reaction chamber under any suitable conditions. For example, the method may be performed in a reaction chamber without opening the reaction chamber. The reaction chamber may be part of an array or reaction chambers. In some embodiments, the steps of the methods may be performed separately in different reaction chambers.

The oligonucleotide of the method may specifically hybridize to any suitable nucleic acid. In some embodiment, the oligonucleotide is capable of specifically hybridizing to a nucleic acid of any one of human parainfluenza virus 1 (HPIV-1), human parainfluenza 2 (HPIV-2), and human parainfluenza 3 (HPIV-3). Nucleic acid of HPIV-1-3 may include DNA, RNA, or cDNA prepared from RNA (e.g., DNA prepared from viral genomic RNA or viral mRNA).

The disclosed methods may be performed with any suitable number of oligonucleotides. In some embodiments of the methods where a plurality of oligonucleotides are used (e.g., two or more oligonucleotides), each oligonucleotide may be labeled with at least one fluorescent dye capable of producing a detectable signal, and each oligonucleotide will be capable of specifically hybridizing to at least one different nucleic acid to be detected in the method. In some embodiments, the plurality of oligonucleotides are labeled with at least one of two different fluorescent dyes. In further embodiments, the plurality of oligonucleotides are labeled with at least one of three different fluorescent dyes or at least one of four different fluorescent dyes.

In some embodiments, the methods are performed with at least twelve (12) oligonucleotides, each of which are specific for at least one nucleic acid in a sample and each of which are labeled with at least one of three different fluorescent dyes. Some oligonucleotides may be labeled with different fluorescent dyes and some oligonucleotides may be labeled with the same fluorescent dye. Where more than one oligonucleotide is labeled with the same fluorescent dye, the nucleic acids that are specifically recognized by the oligonucleotides may have different melting temperatures, which may be used to identify each nucleic acid. Preferably, the nucleic acids have melting temperatures that differ by at least about 1° C., more preferably by at least about 2° C., or even more preferably by at least about 4° C. For example, oligonucleotides labeled with the same fluorescent dye may be specific for nucleic acids which have been amplified from the sample (i.e., "amplicons"). These amplicons may have different melting temperatures that may be used to identify the amplicons. In some embodiments, an amplicon may have a melting temperature that differs by at least about 2 C (preferably at least about 4 C) from the melting temperature of any of the other amplicons that are specifically recognized by any oligonucleotide labeled with the same fluorescent dye. The melting temperature of the amplicons may be determined by using a fluorescent intercalating agent.

Where the method is performed with a plurality of oligonucleotides, each oligonucleotide may be labeled with at least one different fluorescent dye. In some embodiments, each different fluorescent dye emits a signal that can be distinguished from a signal emitted by any other of the different fluorescent dyes that are used to label the oligonucleotides. For example, the different fluorescent dyes may have wavelength emission maximums all of which differ from each other by at least about 5 nm (preferably by least about 10 nm). In some embodiments, each different fluorescent dye is excited by different wavelength energies. For example, the different fluorescent dyes may have wavelength absorption maximums all of which differ from each other by at least about 5 nm (preferably by at least about 10 nm).

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. For example, the fluorescent dye for determining the melting temperature of a nucleic acid may have a wavelength emission maximum that differs from the wavelength emission maximum of any fluorescent dye that is used for labeling an oligonucleotide by at least about 5 nm (preferably by least about 10 nm). In some embodiments, the fluorescent dye for determining the melting temperature of a nucleic acid may be excited by different wavelength energy than any other of the different fluorescent dyes that are used to label the oligonucleotides. For example, the fluorescent dye for determining the melting temperature of a nucleic acid may have a wavelength absorption maximum that differs from the wavelength absorption maximum of any fluorescent dye that is used for labeling an oligonucleotide by at least about 5 nm (preferably by least about 10 nm).

The disclosed methods may include amplifying at least one nucleic acid in the sample. Where the nucleic acid is amplified, the disclosed methods may include detecting the nucleic acid using real-time monitoring.

In some embodiments, the disclosed methods may include detecting nucleic acid of HPIV-1, HPIV-2, and/or HPIV-3. For example, the disclosed methods may include contacting nucleic acids in a sample with oligonucleotides that include at least: (a) a first oligonucleotide labeled with a first fluorescent dye and that is capable of specifically hybridizing to nucleic acid of HPIV-1; (b) a second oligonucleotide labeled with a second fluorescent dye and that is capable of specifically hybridizing to nucleic acid of HPIV-2; and (c) a third oligonucleotide labeled with a third fluorescent dye and that is capable of specifically hybridizing to nucleic acid of HPIV-3. The sample may include multiple nucleic acids of HPIV-1, HPIV-2, and HPIV-3. The multiple nucleic acids may have melting temperatures that can be determined using a fluorescent dye that is different from any fluorescent dye that is used to label the oligonucleotides of the method. For example, the fluorescent dye used to determine the melting temperature may include an intercalating agent. The method may be used to identifying multiple nucleic acids in a sample (e.g., at least 12 different nucleic acids or at least 16 nucleic acids).

DETAILED DESCRIPTION

Disclosed are methods for detecting nucleic acid in a sample. Typically, the methods include detecting multiple signals such as signals emitted from fluorophores.

Unless otherwise stated, the singular forms "a," "an," and "the" include plural reference. Thus, for example, a reference to "an oligonucleotide" includes a plurality of oligonucleotide molecules, and a reference to a "nucleic acid" is a reference to one or more nucleic acids.

As used herein, the term "sample" is used in its broadest sense. A sample may comprise a bodily tissue or a bodily fluid including but not limited to blood (or a fraction of blood such as plasma or serum), lymph, mucus, tears, urine, and saliva. A sample may include an extract from a cell, a chromosome, organelle, or a virus. A sample may comprise DNA (e.g., genomic DNA), RNA (e.g., mRNA), cDNA, any of which may be amplified to provide amplified nucleic acid. A sample may include nucleic acid in solution or bound to a substrate (e.g., as part of a microarray). A sample may comprise material obtained from an environmental locus (e.g., a body of water, soil, and the like) or material obtained from a fomite (i.e., an inanimate object that serves to transfer pathogens from one host to another).

As used herein, "nucleic acid," "nucleotide sequence," or "nucleic acid sequence" refer to a nucleotide, oligonucleotide, polynucleotide, or any fragment thereof and to naturally occurring or synthetic molecules. These phrases also refer to DNA or RNA of genomic or synthetic origin which may be single-stranded or double-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. RNA may be used in the methods described herein and/or may be converted to cDNA by reverse-transcription for use in the methods described herein.

An oligonucleotide is a nucleic acid that includes at least two nucleotides. Oligonucleotides used in the methods disclosed herein typically include at least about ten (10) nucleotides and more typically at least about fifteen (15) nucleotides. Preferred oligonucleotides for the methods disclosed herein include about 10-25 nucleotides. An oligonucleotide may be designed to function as a "probe." A "probe" refers to an oligonucleotide, its complements, or fragments thereof, which is used to detect identical, allelic or related nucleic acid sequences. Probes may include oligonucleotides which have been attached to a detectable label or reporter molecule. Typical labels include fluorescent dyes, radioactive isotopes, ligands, chemiluminescent agents, and enzymes. An oligonucleotide may be designed to function as a "primer." A "primer" is a short nucleic acid, usually a ssDNA oligonucleotide, which may be annealed to a target polynucleotide by complementary base-pairing. The primer may then be extended along the target DNA strand by a DNA polymerase enzyme. Primer pairs can be used for amplification (and identification) of a nucleic acid sequence (e.g., by the polymerase chain reaction (PCR)).

An oligonucleotide may be designed to be specific for a target nucleic acid sequence in a sample. For example, an oligonucleotide may be designed to include "antisense" nucleic acid sequence of the target nucleic acid. As used herein, the term "antisense" refers to any composition capable of base-pairing with the "sense" (coding) strand of a specific target nucleic acid sequence. An antisense nucleic acid sequence may be "complementary" to a target nucleic acid sequence. As used herein, "complementarity" describes the relationship between two single-stranded nucleic acid sequences that anneal by base-pairing. For example, 5'-AGT-3' pairs with its complement, 3'-TCA-5'.

An oligonucleotide that is specific for a target nucleic acid also may be specific for a nucleic acid sequence that has "homology" to the target nucleic acid sequence. As used herein, "homology" refers to sequence similarity or, interchangeably, sequence identity, between two or more polynucleotide sequences or two or more polypeptide sequences. The terms "percent identity" and "% identity" as applied to polynucleotide sequences, refer to the percentage of residue matches between at least two polynucleotide sequences aligned using a standardized algorithm.

An oligonucleotide that is specific for a target nucleic acid will "hybridize" to the target nucleic acid under suitable conditions. As used herein, "hybridization" or "hybridizing" refers to the process by which a oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Equations for calculating $T_m$ and conditions for nucleic acid hybridization are known in the art.

As used herein, "amplification" or "amplifying" refers to the production of additional copies of a nucleic acid sequence. Amplification is generally carried out using polymerase chain reaction (PCR) technologies known in the art.

The term "amplification reaction system" refers to any in vitro means for multiplying the copies of a target sequence of nucleic acid. The term "amplification reaction mixture" refers to an aqueous solution comprising the various reagents used to amplify a target nucleic acid. These include enzymes (e.g., a thermostable polymerase), aqueous buffers, salts, amplification primers, target nucleic acid, and nucleoside triphosphates, and optionally at least one labeled probe and/or optionally at least one agent for determining the melting temperature of an amplified target nucleic acid (e.g., a fluorescent intercalating agent that exhibits a change in fluorescence in the presence of double-stranded nucleic acid).

The amplification methods described herein my include "real-time monitoring" or "continuous monitoring." These terms refer to monitoring multiple times during a cycle of PCR, preferably during temperature transitions, and more preferably obtaining at least one data point in each temperature transition. The term "homogeneous detection assay" is used to describe an assay that includes coupled amplification and detection, which may include "real-time monitoring" or "continuous monitoring."

"Labels" or "reporter molecules" are chemical or biochemical moieties useful for labeling a nucleic acid, amino acid, or antibody. "Labels" and "reporter molecules" include fluorescent agents, chemiluminescent agents, chromogenic agents, quenching agents, radionuclides, enzymes, substrates. cofactors, inhibitors, magnetic particles, and other moieties known in the art. "Labels" or "reporter molecules" are capable of generating a measurable signal and may be covalently or noncovalently joined to an oligonucleotide.

The term "microarray" refers to an arrangement of a plurality of polynucleotides, polypeptides, or other chemical compounds on a substrate. The terms "element" and "array element" refer to a polynucleotide, polypeptide, or other chemical compound having a unique and defined position on a microarray.

As used herein, a "fluorescent dye" or a "fluorophore" is a chemical group that can be excited by light to emit fluorescence. Some suitable fluorophores may be excited by light to emit phosphorescence. Dyes may include acceptor dyes that are capable of quenching a fluorescent signal from a fluorescent donor dye. Dyes that may be used in the disclosed methods include, but are not limited to, the following dyes and/or dyes sold under the following tradenames: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (B isaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NEXT (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; CyS™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DIA (4-Di-16-ASP); Dichlorodihydrofluorescein Diacetate (DCFH); DiD Lipophilic Tracer; DiD (D1IC18(5)); DIDS; Dihydorhodamine 123 (DHR); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow SGF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red;

Nuclear Yellow; Nylosan Brilliant Iavin E8G; Oregon Green; Oregon Green 488-X; Oregon Green™; Oregon Green™488; Oregon Green™500; Oregon Green™514; Pacific Blue; Pararosaniline (Feulgen); PBFI; PE-CyS; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY Quinacrine Mustard; Red 613 [PE-Texas-Red]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

The oligonucleotides of the disclosed methods may be labeled with a donor fluorophore and an acceptor fluorophore such that the acceptor fluorophore is capable of being induced to sensitized emission by the donor fluorophore or is capable of quenching the donor fluorophore. The acceptor fluorophore may be excited to emit fluorescence by FRET. Quenching may include dynamic quenching (e.g. by FRET). static quenching, or both. The oligonucleotides may include a donor fluorophore and an acceptor fluorophore such that the acceptor fluorophore is capable of altering the absorbance spectrum of the donor fluorophore or vice versa.

The oligonucleotides may be labeled with a donor fluorophore and a "dark quencher." Dark quenchers may include black hole quenchers sold under the tradename "BHQ" (e.g., BHQ-0, BHQ-1, BHQ-2, and BHQ-3, Biosearch Technologies, Novato, Calif.). Dark quenchers may include quenchers sold under the tradename "QXL™" (Anaspec, San Jose, Calif.). Dark quenchers may include DNP-type non-fluorophores that include a 2,4-dinitrophenyl group.

The oligonucleotide of the present methods may be labeled with a donor fluorophore and an acceptor fluorophore (or quencher dye) that are present in the oligonucleotides at positions that are suitable to permit FRET (or quenching). For example, the oligonucleotide of the present methods may be labeled with a donor fluorophore and an acceptor fluorophore (or quencher dye) that are present at a selected distance within the oligonucleotide, (e.g., at a distance of about 6-100 angstroms, preferably 15-75 angstroms, more preferably about 30-70 angstroms). The oligonucleotides may be designed to form a hairpin structure to permit FRET (or quenching). Labeled oligonucleotides that are suitable for the present methods may include but are not limited to oligonucleotides designed to function as Taqman® Probes, Molecular Beacon Probes, Amplifluor® Primers, Scorpion® Primers, and Lux™ Primers.

The oligonucleotides of the present methods may function as probes. For example, the oligonucleotides may be labeled with a fluorophore that emits a signal after the oligonucleotide hybridizes to a target nucleic acid. Fluorescence may be induced (e.g., by FRET between and acceptor and a donor) or fluorescence may be dequenched. Such probes are known in the art (e.g., Molecular Beacons). The oligonucleotide may emit a detectable signal after the oligonucleotide hybridizes to a target nucleic acid and further is hydrolyzed after the target nucleic acid is amplified (e.g., by a 5'→3' exonuclease activity of a polymerase used for PCR amplification such as Taq polymerase). As such, a nucleotide labeled with a fluorescent dye may be hydrolyzed from the hybridized oligonucleotide and the fluorescent dye may exhibit fluorescence dequenching. Suitable probes are known in the art (e.g., Taqman® Probes).

The oligonucleotides of the present methods may function as primers. In some embodiments, the oligonucleotide may form a hairpin structure that is altered after the oligonucleotide hybridizes to a target nucleic acid and the target nucleic acid is amplified using the oligonucleotide as a primer. The oligonucleotide may emit a detectable signal after the oligonucleotide is incorporated in an amplified product as a primer (e.g., by fluorescence induction or fluorescence dequenching). Such primers are know in the art (e.g., Amplifluor® Primers, Scorpion® Primers and Lux™ Primers). The fluorophore used to label the oligonucleotide may emit a signal when intercalated in double-stranded nucleic acid. As such, the fluorophore may emit a signal after the oligonucleotide is used as a primer for amplifying the nucleic acid.

In the disclosed methods, the fluorescent dyes used to label the oligonucleotides and any fluorescent dye used to determine the melting temperature of a nucleic acid may be selected for having suitable maximum emission wavelengths and/or suitable maximum absorption wavelengths. It may be desirable to select different fluorescent dyes that emit signals that are easily detected and distinguished. For example, the different fluorescent dyes may have wavelength emission maximums all of which differ from each other by at least about 5 nm (preferably by least about 10 nm). In some embodiments, each different fluorescent dye may be excited by different wavelength energies which differ from each other by at least about 5 nm (preferably by least about 10 nm). Table 1 provides a non-exclusive listing of fluorescent dyes (i.e., fluorophores) which may be used in the present methods (e.g., to label oligonucleotides and/or to determine the melting temperature of nucleic acid) and indicates the absorption maximum wavelength (nm) and emission maximum wavelength (nm) for each fluorescent dye.

TABLE 1

| FLUOROPHORE | ABSORPTION (nm) | EMISSION (nm) |
|---|---|---|
| 1,5 IAEDANS | 336 | 490 |
| 1,8-ANS | 372 | 480 |
| 4-Methylumbelliferone | 385 | 502 |
| 5-carboxy-2,7-dichlorofluorescein | 504 | 529 |
| 5-Carboxyfluorescein (5-FAM) | 492 | 518 |
| 5-Carboxynapthofluorescein (pH 10) | 512/598 | 563/668 |
| 5-Carboxytetramethylrhodamine (5-TAMRA) | 542 | 568 |
| 5-FAM (5-Carboxyfluorescein) | 492 | 518 |
| 5-HAT (Hydroxy Tryptamine) | 370-415 | 520-540 |
| 5-Hydroxy Tryptamine (HAT) | 370-415 | 520-540 |
| 5-ROX (carboxy-X-rhodamine) | 567, 578 | 591, 604 |
| 5-TAMRA (5-Carboxytetramethylrhodamine) | 542, 548 | 552, 568 |
| 6-Carboxyrhodamine 6G | 518 | 543 |
| 6-CR 6G | 518 | 543 |
| 6-JOE | 520 | 548 |
| 7-Amino-4-methylcoumarin | 351 | 430 |
| 7-Aminoactinomycin D (7-AAD) | 546 | 647 |
| 7-Hydroxy-4-methylcoumarin | 360 | 449, 455 |
| 9-Amino-6-chloro-2-methoxyacridine | 412, 430 | 471, 474 |
| ABQ | 344 | 445 |
| Acid Fuchsin | 540 | 630 |
| ACMA (9-Amino-6-chloro-2-methoxyacridine) | 412, 430 | 471, 474 |
| Acridine Orange + DNA | 502 | 526 |
| Acridine Orange + RNA | 460 | 650 |
| Acridine Orange, both DNA & RNA | 440-480 | 520-650 |
| Acridine Red | 455-600 | 560-680 |
| Acridine Yellow | 470 | 550 |
| Acriflavin | 436 | 520 |
| Acriflavin Feulgen SITSA | 355-425 | 460 |
| Alexa Fluor 350 ™ | 342, 346 | 441, 442 |
| Alexa Fluor 430 ™ | 431 | 540 |
| Alexa Fluor 488 ™ | 495, 492 | 519, 520 |
| Alexa Fluor 532 ™ | 531, 532 | 553, 554 |
| Alexa Fluor 546 ™ | 556, 557 | 572, 573 |
| Alexa Fluor 568 ™ | 577, 578 | 603 |
| Alexa Fluor 594 ™ | 590, 594 | 617, 618 |
| Alexa Fluor 633 ™ | 632 | 650 |
| Alexa Fluor 647 ™ | 647 | 666 |
| Alexa Fluor 660 ™ | 668 | 698 |
| Alexa Fluor 680 ™ | 679 | 702 |
| Alizarin Complexon | 530-560, 580 | 580, 624-645 |
| Alizarin Red | 530-560 | 580 |
| Allophycocyanin (APC) | 630, 645 | 655, 660 |
| AMC, AMCA-S | 345 | 445 |
| AMCA (Aminomethylcoumarin) | 345, 347 | 425, 444 |
| AMCA-X | 353 | 442 |
| Aminoactinomycin D | 555 | 655 |
| Aminocoumarin | 346, 350 | 442, 445 |
| Aminomethylcoumarin (AMCA) | 345, 347 | 425, 444 |
| Anthrocyl stearate | 360-381 | 446 |
| APC (Allophycocyanin) | 630, 645 | 655, 660 |
| APC-Cy7 | 625-650 | 755 |
| APTRA-BTC = Ratio Dye, $Zn^{2+}$ | 466/380 | 520/530 |
| APTS | 424 | 505 |
| Astrazon Brilliant Red 4G | 500 | 585 |
| Astrazon Orange R | 470 | 540 |
| Astrazon Red 6B | 520 | 595 |
| Astrazon Yellow 7 GLL | 450 | 480 |
| Atabrine | 436 | 490 |
| ATTO-TAG ™ CBQCA | 465 | 560 |
| ATTO-TAG ™ FQ | 486 | 591 |
| Auramine | 460 | 550 |
| Aurophosphine G | 450 | 580 |
| Aurophosphine | 450-490 | 515 |
| BAO 9 (Bisaminophenyloxadiazole) | 365 | 395 |
| BCECF (high pH) | 492, 503 | 520, 528 |
| BCECF (low pH) | 482 | 520 |
| Berberine Sulphate | 430 | 550 |
| Beta Lactamase | 409 | 447, 520 |
| BFP blue shifted GFP (Y66H) | 381, 382, 383 | 445, 447, 448 |
| Bimane | 398 | 490 |
| Bisbenzamide | 360 | 461 |
| Bisbenzimide (Hoechst) | 360 | 461 |
| bis-BTC = Ratio Dye, $Zn^{2+}$ | 455/405 | 529/505 |
| Blancophor FFG | 390 | 470 |
| Blancophor SV | 370 | 435 |
| BOBO ™-1 | 462 | 481 |
| BOBO ™-3 | 570 | 602 |
| Bodipy 492/515 | 490 | 515 |
| Bodipy 493/503 | 533 | 549 |
| Bodipy 500/510 | 509 | 515 |
| Bodipy 505/515 | 502 | 510 |
| Bodipy 530/550 | 528 | 547 |
| Bodipy 542/563 | 543 | 563 |
| Bodipy 558/568 | 558 | 569 |
| Bodipy 564/570 | 564 | 570 |
| Bodipy 576/589 | 579 | 590 |
| Bodipy 581/591 | 584 | 592 |
| Bodipy 630/650-X | 625 | 642 |
| Bodipy 650/665-X | 647 | 665 |
| Bodipy 665/676 | 605 | 676 |
| Bodipy Fl | 504, 505 | 511, 513 |
| Bodipy FL ATP | 505 | 514 |
| Bodipy Fl-Ceramide | 505 | 511 |
| Bodipy R6G SE | 528 | 547 |
| Bodipy TMR | 542 | 574 |
| Bodipy TMR-X conjugate | 544 | 573 |
| Bodipy TMR-X, SE | 544 | 570 |
| Bodipy TR | 589 | 617 |
| Bodipy TR ATP | 591 | 620 |
| Bodipy TR-X SE | 588 | 616 |
| BO-PRO ™-1 | 462 | 481 |
| BO-PRO ™-3 | 544 | 570 |
| Brilliant Sulphoflavin FF | 430 | 520 |
| BTC-Ratio Dye $Ca^{2+}$ | 464/401 | 533/529 |
| BTC-5N-atio Dye, $Zn^{2+}$ | 459/417 | 517/532 |
| Calcein | 494 | 517 |
| Calcein Blue | 373 | 440 |
| Calcium Crimson ™ | 588, 589 | 611, 615 |
| Calcium Green | 501, 506 | 531 |
| Calcium Green-1 $Ca^{2+}$ Dye | 506 | 531 |
| Calcium Green-2 $Ca^{2+}$ | 506/503 | 536 |
| Calcium Green-5N $Ca^{2+}$ | 506 | 532 |
| Calcium Green-C18 $Ca^{2+}$ | 509 | 530 |
| Calcium Orange | 549 | 575, 576 |
| Calcofluor White | 385, 395, 405 | 437, 440, 445 |
| Carboxy-X-rhodamine (5-ROX) | 576 | 601 |
| Cascade Blue ™ | 377, 398, 399 | 420, 423 |
| Cascade Yellow | 399, 400 | 550, 552 |
| Catecholamine | 410 | 470 |
| CFDA | 494 | 520 |
| CFP - Cyan Fluorescent Protein | 430, 433, 436, (453) | 474, 475, 476, (501) |
| Chlorophyll | 480 | 650 |
| Chromomycin A | 436-460 | 470 |
| Chromomycin A | 445 | 575 |
| CL-NERF (Ratio Dye, pH) | 504/514 | 540 |
| CMFDA | 494 | 520 |
| Coelenterazine $Ca^{2+}$ Dye, bioluminescence | (429) | 465 |
| Coelenterazine cp ($Ca^{2+}$ Dye,) | (430) | 442 |
| Coelenterazine f | (437) | 473 |
| Coelenterazine h | (437) | 464 |
| Coelenterazine hcp | (433) | 444 |
| Coelenterazine n | (431) | 467 |
| Coelenterazine O | 460 | 575 |
| Coumarin Phalloidin | 387 | 470 |
| CPM Methylcoumarin | 384 | 469 |
| CTC | 400-450 | 602 |
| Cy2 ™ | 489 | 506 |
| Cy3.1 8 | 554 | 568 |
| Cy3.5 ™ | 581 | 598 |
| Cy3 ™ | 514, 552, 554 | 566, 570 |
| Cy5.1 8 | 649 | 666 |
| Cy5.5 ™ | 675 | 695 |
| Cy5 ™ | 649 | 666, 670 |
| Cy7 ™ | 710, 743 | 767, 805 |

TABLE 1-continued

| FLUOROPHORE | ABSORPTION (nm) | EMISSION (nm) |
|---|---|---|
| Cyan GFP | 433 (453) | 475 (501) |
| cyclic AMP Fluorosensor (FiCRhR) | 500 | 517 |
| CyQuant Cell Proliferation Assay | 480 | 520 |
| Dansyl | 340 | 578 |
| Dansyl Amine | 337 | 517 |
| Dansyl Cadaverine | 335 | 518 |
| Dansyl Chloride | 372 | 518 |
| Dansyl DHPE | 336 | 517 |
| DAPI | 359 | 461 |
| Dapoxyl | 403 | 580 |
| Dapoxyl 2 | 374 | 574 |
| Dapoxyl 3 | 373 | 574 |
| DCFDA | 504 | 529 |
| DCFH (Dichlorodihydrofluorescein Diacetate) | 505 | 535 |
| DDAO | 463 | 607 |
| DHR (Dihydorhodamine 123) | 505 | 534 |
| Di-4-ANEPPS | 496 | 705 |
| Di-8-ANEPPS (non-ratio) | 488, 498 | 605, 713 |
| DiA (4-Di-16-ASP) | 456 | 591 |
| Dichlorodihydrofluorescein Diacetate (DCFH) | 505 | 535 |
| DiD-Lipophilic Tracer | 644 | 665 |
| DiD (DiIC18(5)) | 644 | 665 |
| DIDS | 341 | 415 |
| Dihydrorhodamine 123 (DHR) | 505 | 535 |
| DiI (DiIC18(3)) | 549, 551 | 565 |
| DiO (DiOC18(3)) | 484, 487 | 501, 502 |
| DiR | 748 | 780 |
| DiR (DiIC18(7)) | 750 | 779 |
| DM-NERF (high pH) | 497/510 | 540 |
| Dopamine | 340 | 490-520 |
| DsRed | 558 | 583 |
| DTAF | 494 | 520 |
| DY-630-NHS | 621 | 660 |
| DY-635-NHS | 634 | 664 |
| EBFP | 383 | 447 |
| ECFP | 436 | 474 |
| EGFP | 488, 498 | 507, 516 |
| ELF 97 | 345 | 530 |
| Eosin | 524 | 545 |
| Erythrosin | 529, 532 | 554, 555 |
| Erythrosin ITC | 529 | 555 |
| Ethidium Bromide | 510, 523 | 595, 605 |
| Ethidium homodimer-1 (EthD-1) | 528 | 617 |
| Euchrysin | 430 | 540 |
| EYFP | 513, 520 | 527, 532 |
| Fast Blue | 360 | 440 |
| FDA | 494 | 520 |
| Feulgen (Pararosaniline) | 570 | 625 |
| FIF (Formaldehyd Induced Fluorescence) | 405 | 433 |
| FITC | 490, 494 | 520, 525 |
| FITC Antibody | 493 | 517 |
| Flazo Orange | 375-530 | 612 |
| Fluo-3 | 480-506, 506 | 520, 527 |
| Fluo-4 | 494 | 516 |
| Fluorescein (FITC) | 490, 494 | 520, 525 |
| Fluorescein Diacetate | 494 | 520 |
| Fluoro-Emerald | 495 | 524 |
| Fluoro-Gold (Hydroxystilbamidine) | 361 | 536 |
| Fluor-Ruby | 555 | 582 |
| FluorX | 494 | 520 |
| FM 1-43™ | 479 | 598 |
| FM 4-46 | 515 | 640 |
| Fura Red™ (high pH) | 572 | 657 |
| Fura-2, high calcium | 335 | 505 |
| Fura-2, low calcium | 363 | 512 |
| Genacryl Brilliant Red B | 520 | 590 |
| Genacryl Brilliant Yellow 10GF | 430 | 485 |
| Genacryl Pink 3G | 470 | 583 |
| Genacryl Yellow 5GF | 430 | 475 |
| GFP (S65T) | 498 | 516 |
| GFP red shifted (rsGFP) | 498 | 516 |
| GFP wild type, non-UV excitation (wtGFP) | 475 | 509 |
| GFP wild type, UV excitation (wtGFP) | 395 | 509 |
| GFPuv | 385 | 508 |
| Gloxalic Acid | 405 | 460 |
| Granular Blue | 355 | 425 |
| Haematoporphyrin | 530-560 | 580 |
| Hoechst 33258 | 345 | 487 |
| Hoechst 33342 | 347 | 483 |
| Hoechst 34580 | 392 | 440 |
| HPTS | 355 | 465 |
| Hydroxycoumarin | 325-360 | 386-455 |
| Hydroxystilbamidine (FluoroGold) | 361 | 536 |
| Hydroxytryptamine | 400 | 530 |
| Indo-1, high calcium | 330 | 401 |
| Indo-1, low calcium | 346 | 475 |
| Indodicarbocyanine (DiD) | 644 | 665 |
| Indotricarbocyanine (DiR) | 748 | 780 |
| Intrawhite Cf | 360 | 430 |
| JC-1 | 514 | 529 |
| JO-JO-1 | 530 | 545 |
| JO-PRO-1 | 532 | 544 |
| LaserPro | 795 | 812 |
| Laurodan | 355 | 460 |
| LDS 751 (DNA) | 543 | 712 |
| LDS 751 (RNA) | 590 | 607 |
| Leucophor PAF | 370 | 430 |
| Leucophor SF | 380 | 465 |
| Leucophor WS | 395 | 465 |
| Lissamine Rhodamine | 572, 577 | 591, 592 |
| Lissamine Rhodamine B | 577 | 592 |
| LOLO-1 | 566 | 580 |
| LO-PRO-1 | 568 | 581 |
| Lucifer Yellow | 425, 428 | 528, 536, 540 |
| Lyso Tracker Blue | 373 | 422 |
| Lyso Tracker Blue-White | 466 | 536 |
| Lyso Tracker Green | 504, 534 | 511, 551 |
| Lyso Tracker Red | 490 | 516 |
| Lyso Tracker Yellow | 551 | 576 |
| LysoSensor Blue | 374 | 424 |
| LysoSensor Green | 442 | 505 |
| LysoSensor Yellow/Blue | 384 | 540 |
| Mag Green | 507 | 531 |
| Magdala Red (Phloxin B) | 524 | 600 |
| Mag-Fura Red | 483/427 | 659/631 |
| Mag-Fura-2 | 369/329, 369/330 | 508, 511/491 |
| Mag-Fura-5 | 369/330, 369/332 | 505/500, 505/482 |
| Mag-Indo-1 | 349/328, 349/330 | 480/390, 480/417 |
| Magnesium Green | 506, 507 | 531 |
| Magnesium Orange | 550 | 575 |
| Marina Blue | 362 | 459 |
| Maxilon Brilliant Flavin 10 GFF | 450 | 495 |
| Maxilon Brilliant Flavin 8 GFF | 460 | 495 |
| Merocyanin | 555 | 578 |
| Methoxycoumarin | 360 | 410 |
| Mitotracker Green FM | 490 | 516 |
| Mitotracker Orange | 551 | 576 |
| Mitotracker Red | 578 | 599 |
| Mitramycin | 450 | 470 |
| Monobromobimane | 398 | 490 |
| Monobromobimane (mBBr-GSH) | 398 | 500 |
| Monochlorobimane | 380 | 461 |
| MPS (Methyl Green Pyronine Stilbene) | 364 | 395 |
| NBD | 466 | 539 |
| NBD Amine | 450 | 530 |
| Nile Red | 515-555, 559 | 590, 640 |
| Nitrobenzoxadidole | 465 | 510-650 |
| Noradrenaline | 340 | 490-520 |
| Nuclear Fast Red | 289-530 | 580 |
| Nuclear Yellow | 365 | 495 |
| Nylosan Brilliant Iavin E8G | 460 | 510 |
| Oregon Green | 503 | 522 |
| Oregon Green 488-X | 494 | 517 |
| Oregon Green™ | 503 | 522 |
| Oregon Green™ 488 | 490, 493 | 514, 520 |
| Oregon Green™ 500 | 497 | 517 |

TABLE 1-continued

| FLUOROPHORE | ABSORPTION (nm) | EMISSION (nm) |
|---|---|---|
| Oregon Green ™ 514 | 506 | 526 |
| Pacific Blue | 405 | 455 |
| Pararosaniline (Feulgen) | 570 | 625 |
| PBFI | 340/380 | 420 |
| PE-Cy5 | 488 | 670 |
| PE-Cy7 | 488 | 755, 767 |
| PerCP | 488 | 675 |
| PerCP-Cy5.5 | 488 | 710 |
| PE-TexasRed [Red 613] | 488 | 613 |
| Phloxin B (Magdala Red) | 524 | 600 |
| Phorwite AR | 360 | 430 |
| Phorwite BKL | 370 | 430 |
| Phorwite Rev | 380 | 430 |
| Phorwite RPA | 375 | 430 |
| Phosphine 3R | 465 | 565 |
| PhotoResist | 365 | 610 |
| Phycoerythrin B [PE] | 546-565 | 575 |
| Phycoerythrin R [PE] | 565 | 578 |
| PKH26 (Sigma) | 551 | 567 |
| PKH67 | 496 | 520 |
| PMIA | 341 | 376 |
| Pontochrome Blue Black | 535-553 | 605 |
| POPO-1 | 433 | 457 |
| POPO-3 | 533 | 574 |
| PO-PRO-1 | 435 | 455 |
| PO-PRO-3 | 539 | 567 |
| Primuline | 410 | 550 |
| Procion Yellow | 470 | 600 |
| Propidium Iodid (PI) | (305), 536, 538 | 617 |
| PyMPO | 412, 415 | 561, 564, 570 |
| Pyrene | 360 | 387 |
| Pyronine | 410 | 540 |
| Pyronine B | 540-590 | 560-650 |
| Pyrozal Brilliant Flavin 7GF | 365 | 495 |
| Quinacrine Mustard | 440 | 510 |
| Red 613 [PE-TexasRed] | 488 | 613 |
| Resorufin | 571 | 584, 585 |
| RH 414 | 532 | 716 |
| Rhod-2 | 552 | 576 |
| Rhodamine | 550 | 573 |
| Rhodamine 110 | 496, 497 | 520 |
| Rhodamine 123 | 507 | 529 |
| Rhodamine 5 GLD | 470 | 565 |
| Rhodamine 6G | 525 | 555 |
| Rhodamine B | 540 | 625 |
| Rhodamine B 200 | 523-557 | 595 |
| Rhodamine B extra | 550 | 605 |
| Rhodamine BB | 540 | 580 |
| Rhodamine BG | 540 | 572 |
| Rhodamine Green | 502 | 527 |
| Rhodamine Phallicidine | 558, 542 | 575, 565 |
| Rhodamine Phalloidine | 542 | 565 |
| Rhodamine Red | 570 | 590 |
| Rhodamine WT | 530 | 555 |
| Rose Bengal | 525, 540 | 550-600 |
| R-phycoerythrin (PE) | 565 | 578 |
| rsGFP | 473 | 509 |
| S65A | 471 | 504 |
| S65C | 479 | 507 |
| S65L | 484 | 510 |
| S65T | 488 | 511 |
| Sapphire GFP | 395 | 511 |
| SBFI | 340/380 | 420 |
| Serotonin | 365 | 520-540 |
| Sevron Brilliant Red 2B | 520 | 595 |
| Sevron Brilliant Red 4G | 500 | 583 |
| Sevron Brilliant Red B | 530 | 590 |
| Sevron Orange | 440 | 530 |
| Sevron Yellow L | 430 | 490 |
| sgBFP ™ | 387 | 450 |
| sgBFP ™ (super glow BFP) | 387 | 450 |
| sgGFP ™ | 474 | 488 |
| sgGFP ™ (super glow GFP) | 474 | 509 |
| SITS | 336 | 436 |
| SITS (Primuline) | 395-425 | 450 |
| SITS (Stilbene Isothiosulphonic Acid) | 365 | 460 |
| SNAFL calcein | 506/535 | 535/620 |
| SNAFL-1 | 508/540 | 543/623 |
| SNAFL-2 | 514/543 | 546/630 |
| SNARF calcein | 552/574 | 590/629 |
| SNARF1 | 576/548 | 635/587 |
| Sodium Green | 506, 507 | 532 |
| SpectrumAqua | 433,/53 | 480/55 |
| SpectrumGreen | 497/30, 509/31 | 538/44, 524/56 |
| SpectrumOrange | 559/38, 560 | 588/48 |
| Spectrum Red | 587, 587/35 | 612, 612/51 |
| SPQ (6-methoxy-N-(3-sulfopropyl)quinolinium) | 344 | 443 |
| Stilbene | 335 | 440 |
| Sulphorhodamine B can C | 520 | 595 |
| Sulphorhodamine G Extra | 470 | 570 |
| SYTO 11 | 508, 510 | 527, 530 |
| SYTO 12 | 499, 500 | 522, 519 |
| SYTO 13 | 488, 491 | 509, 514 |
| SYTO 14 | 517, 521 | 549, 547 |
| SYTO 15 | 516, 518 | 546, 555 |
| SYTO 16 | 488, 494 | 518, 525 |
| SYTO 17 | 621 | 634 |
| SYTO 18 | 490, 493 | 507, 527 |
| SYTO 20 | 512 | 530 |
| SYTO 21 | 494 | 517 |
| SYTO 22 | 515 | 535 |
| SYTO 23 | 499 | 520 |
| SYTO 24 | 490 | 515 |
| SYTO 25 | 521 | 556 |
| SYTO 40 | 420 | 441 |
| SYTO 41 | 430 | 454 |
| SYTO 42 | 433 | 460 |
| SYTO 43 | 436 | 467 |
| SYTO 44 | 446 | 471 |
| SYTO 45 | 452 | 484 |
| SYTO 59 | 622 | 645 |
| SYTO 60 | 652 | 678 |
| SYTO 61 | 628 | 645 |
| SYTO 62 | 652 | 676 |
| SYTO 63 | 657 | 673 |
| SYTO 64 | 599 | 619 |
| SYTO 80 | 531 | 545 |
| SYTO 81 | 530 | 544 |
| SYTO 82 | 541 | 560 |
| SYTO 83 | 543 | 559 |
| SYTO 84 | 567 | 582 |
| SYTO 85 | 567 | 583 |
| SYTOX Blue | 445 | 470 |
| SYTOX Green | 504 | 523 |
| SYTOX Orange | 547 | 570 |
| Tetracycline | 390-425 | 525-560 |
| Tetramethylrhodamine (TRITC) | 555 | 576 |
| Texas Red ™ | 595 | 620 |
| Texas Red-X ™ conjugate | 595 | 615 |
| Thiadicarbocyanine (DiSC3) | 651, 653 | 674, 675 |
| Thiazine Red R | 596 | 615 |
| Thiazole Orange | 510 | 530 |
| Thioflavin 5 | 430 | 550 |
| Thioflavin S | 430 | 550 |
| Thioflavin TCN | 350 | 460 |
| Thiolyte | 370-385 | 477-488 |
| Thiozole Orange | 453 | 480 |
| Tinopol CBS (Calcofluor White) | 390 | 430 |
| TMR | 550 | 573 |
| TO-PRO-1 | 515 | 531 |
| TO-PRO-3 | 644 | 657 |
| TO-PRO-5 | 747 | 770 |
| TOTO-1 | 514 | 531, 533 |
| TOTO-3 | 642 | 660 |
| TriColor (PE-Cy5) | (488) 650 | 667 |
| TRITC | 550 | 573 |
| True Blue | 365 | 425 |
| TruRed | 490 | 695 |
| Ultralite | 656 | 678 |
| Uranine B | 420 | 520 |
| Uvitex SFC | 365 | 435 |
| wt GFP | 395 (475) | 508 |

TABLE 1-continued

| FLUOROPHORE | ABSORPTION (nm) | EMISSION (nm) |
|---|---|---|
| WW 781 | 605 | 639 |
| X-Rhodamine | 580 | 605 |
| XRITC | 582 | 601 |
| Xylene Orange | 546 | 580 |
| Y66F | 360 | 508 |
| Y66H | 360 | 442 |
| Y66W | 436 | 485 |
| Yellow GFP | 513 | 527 |
| YFP | 513, 520 | 527, 532 |
| YO-PRO-1 | 491 | 506 |
| YO-PRO-3 | 613 | 629 |
| YOYO-1 | 491 | 508, 509 |
| YOYO-3 | 612 | 631 |

The disclosed methods may include using an intercalating agent (which may include a fluorescent dye) to determine the melting temperature of a nucleic acid in a sample. As used herein, an "intercalating agent" is an agent (e.g., a chemical) that can insert itself between stacked bases at the center of double-stranded DNA. "Intercalation" or "intercalating" is the act of inserting or being inserted between stacked bases at the center of double-stranded DNA. An intercalating agent may exhibit a change in fluorescence when intercalated. A "change in fluorescence" may include a spectrum shift. For example, an intercalating agent may exhibit a spectrum shift (to the left or right) in maximum absorbance wavelength and/or maximum emission wavelength when intercalated in double-stranded DNA. A "change in fluorescence" may include an increase or a decrease in fluorescence intensity.

Intercalating agents that exhibit a change in fluorescence may be used to determine the melting temperature of a nucleic acid by monitoring fluorescence of the intercalating agent at a gradient of temperatures. In which case, the intercalating agent may exhibit a change in fluorescence at the melting temperature of the nucleic acid. Examples of intercalating agents that are suitable for the disclosed methods include but are not limited to SYBR™ Green 1 dye, SYBR dyes. Pico Green, SYTO dyes, SYTOX dyes, ethidium bromide, ethidium homodimer-1, ethidium homodimer-2, ethidium derivatives, acridine, acridine orange, acridine derivatives. ethidium-acridine heterodimer, ethidium monoazide, propidium iodide, cyanine monomers, 7-aminoactinomycin D, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5. PO-PRO-1, BO-PRO-1, PO-PRO-3, BO-PRO-3, LO-PRO-1, and JO-PRO-1.

EXAMPLE

Twelve (12) different sets of specific primers and probes for twelve (12) different target nucleic acids (T1-T12) are used in an amplification reaction. Each probe is labeled with one of three different fluorescent dyes whose signals are capable of being detected and distinguished (e.g., TET™, VIC®, and NED™, respectively). If present in the sample, a target nucleic acid is amplified and can be detected by observing a signal from one of the fluorescent dyes.

Because more than one probe will be labeled with the same fluorescent dye, each amplified target nucleic acid is identified further based on melting temperature. Each of any amplified target nucleic acids that are recognized by probes labeled with the same fluorescent dye are designed to have different melting temperatures (based on GC content and product length). The different melting temperatures can be used further to identify the amplified target nucleic acid using $T_m$ analysis with a fluorescent intercalating agent that exhibits a change in fluorescence when the amplified target nucleic acid is melted (e.g., SYBR™ Green I dye). Table 2 describes fluorescent dye labels for probes specific for target nucleic acids T1-T12, and also shows $T_m$ values for amplified target nucleic acid products.

TABLE 2

Fluorescent Dye Labels and $T_m$ values for 12 Amplified Target Nucleic Acids in a Multiplex Reaction

| Target Number | Probe-Dye | $T_m$ of Amplified Product |
|---|---|---|
| T1 | P1-TET ™ | 77° C. |
| T2 | P2-TET ™ | 81° C. |
| T3 | P3-TET ™ | 85° C. |
| T4 | P4-TET ™ | 89° C. |
| T5 | P5-VIC ® | 77° C. |
| T6 | P6-VIC ® | 81° C. |
| T7 | P7-VIC ® | 85° C. |
| T8 | P8-VIC ® | 89° C. |
| T9 | P9-NED ™ | 77° C. |
| T10 | P10-NED ™ | 81° C. |
| T11 | P11-NED ™ | 85° C. |
| T12 | P12-NED ™ | 89° C. |

Four dyes are used for detection: Color 1 (SYBR™ Green I dye) is used for melting temperature analysis; Color 2 (TET™ Dye) is used to label probes P1-P4 which are specific for targets T1-T4, respectively; Color 3 (VIC® Dye) is used to label probes P5-P8 which are specific for targets T5-T8, respectively; Color 4 (NED™ Dye) is used to label probes P9-P12 which are specific for targets T9-T12, respectively.

Upon amplification of a product, a color associated with a particular probe is observed. For example, where one of targets T1-T4 is amplified, a fluorescent signal from the TET™ dye is observed. A melting temperature analysis then is used to further discriminate the amplified target nucleic acid. The temperature of the amplification reaction mixture is increased until a decrease in fluorescence from SYBR™ Green I dye is observed to determine a melting temperature of the amplified product. An observed TET™ dye signal for an amplified product having a $T_m$ of 81° C. indicates that the target nucleic acid is T2.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

All references, patents, and/or applications cited in the specification are incorporated by reference in their entireties, including any tables and figures, to the same extent as if each reference had been incorporated by reference in its entirety individually.

What is claimed is:

1. A method for identifying a nucleic acid in a sample, comprising:
   (a) providing a sample nucleic acid bound to a solid substrate;
   (b) contacting the sample nucleic acid with an oligonucleotide that is specific for the sample nucleic acid and is labeled with at least a first fluorescent dye;
   (c) contacting the sample nucleic acid with a second fluorescent dye that is different from the first fluorescent dye, wherein said second fluorescent dye interacts with the sample nucleic acid and is not covalently linked to an oligonucleotide;
   (d) amplifying the sample nucleic acid;
   (e) detecting the sample nucleic acid by observing fluorescence from the first fluorescent dye after said oligonucleotide hybridizes to said amplified sample nucleic acid; and
   determining the melting temperature of the amplified sample nucleic acid by measuring the fluorescence of the second fluorescent dye, and wherein there is no fluorescence resonance energy transfer (FRET) between the first fluorescent dye that labels the oligonucleotide and the second fluorescent dye.

2. The method of claim 1, wherein step (b) and step (c) are performed concurrently.

3. The method of claim 1, wherein step (c) is performed before step (b).

4. The method of claim 1, wherein step (d) is performed before or during step (b).

5. The method of claim 1, wherein step (e) is performed during step (d).

6. The method of claim 1, wherein the oligonucleotide is used as a primer for amplifying the sample nucleic acid.

7. The method of claim 1, wherein the oligonucleotide is used as a probe for said amplified sample nucleic acid.

8. The method of claim 1, wherein the oligonucleotide further is labeled with a quencher dye.

9. The method of claim 1, wherein the oligonucleotide further is labeled with a fluorescent donor dye, and the first fluorescent dye and the fluorescent donor dye exhibit fluorescence resonance energy transfer (FRET).

10. The method of claim 1, wherein the second fluorescent dye for determining the melting temperature of the detected sample nucleic acid comprises an intercalating agent that exhibits a change in fluorescence when intercalated in double-stranded nucleic acid.

11. A method for identifying one of two or more sample nucleic acids that are in a sample, comprising:
    (a) providing two or more sample nucleic acids bound to a solid substrate;
    (b) contacting the sample nucleic acids with two or more oligonucleotides each of which is specific for a different one of said two or more sample nucleic acids and each of which is labeled with at least one fluorescent dye;
    (c) contacting the sample nucleic acids with a different fluorescent dye from the fluorescent dye used to label the two or more oligonucleotides, wherein said different fluorescent dye interacts with the two or more sample nucleic acids and is not covalently linked to an oligonucleotide;
    (d) amplifying one of the two or more nucleic acids; and
    (e) detecting said amplified sample nucleic acids if present in the sample by observing fluorescence from the fluorescent dye of at least one of the two or more oligonucleotides after said oligonucleotide hybridizes to said amplified sample nucleic acids; and determining the melting temperature of said amplified sample nucleic acids by measuring the fluorescence of the different fluorescent dye interacting with said amplified sample nucleic acids, and wherein there is no fluorescence resonance energy transfer (FRET) between the fluorescent dyes that label the two or more nucleic acids and the fluorescent dye not covalently linked to an oligonucleotide.

12. The method of claim 11, wherein step (b) and step (c) are performed concurrently.

13. The method of claim 11, wherein step (c) is performed before step (b).

14. The method of claim 11, wherein step (d) is performed before or during step (c).

15. The method of claim 11, wherein step (e) is performed during step (d).

16. The method of claim 11, wherein at least one of the two or more oligonucleotides is used as a primer for amplifying at least one sample nucleic acid.

17. The method of claim 11, wherein at least one of the two or more oligonucleotides is used as a probe for at least one amplified sample nucleic acid.

18. The method of claim 11, wherein each of the two or more oligonucleotides further is labeled with a quencher dye.

19. The method of claim 11, wherein said oligonucleotide comprises a probe that is hydrolyzed during amplification of said nucleic acid and said fluorescence is observed after said probe is hydrolyzed.

20. The method of claim 11, wherein each of the two or more oligonucleotides further is labeled with a second fluorescent dye, and the fluorescent dye and the second fluorescent dye that are used to label each of the two or more oligonucleotides exhibit fluorescence resonance energy transfer (FRET).

21. The method of claim 11, wherein the different fluorescent dye that is used for determining the melting temperature of the amplified nucleic acid comprises an intercalating agent that exhibits a change in fluorescence when intercalated in double-stranded nucleic acid.

22. The method of claim 11, wherein the two or more oligonucleotides comprise at least twelve different oligonucleotides that are specific for at least twelve different sample nucleic acids potentially in the sample and each of the twelve oligonucleotides is labeled with at least one of three different fluorescent dyes.

23. The method of claim 11, wherein the amplified nucleic acid has a melting temperature that differs by at least about 2° C. from any other amplified sample nucleic acid if the two or more oligonucleotides that are specific for each amplified sample nucleic acid are labeled with the same fluorescent dye.

24. The method of claim 11, wherein the amplified nucleic acid has a melting temperature that differs by at least about 4° C. from any other amplified sample nucleic acid if the two or more oligonucleotides that are specific for each amplified sample nucleic acid are labeled with the same fluorescent dye.

* * * * *